United States Patent [19]

Loveless et al.

[11] Patent Number: 4,594,469

[45] Date of Patent: Jun. 10, 1986

[54] METHOD FOR THE OLIGOMERIZATION OF ALPHA-OLEFINS

[75] Inventors: Frederick C. Loveless, Cheshire; Aspet V. Merijanian, Middlebury; David J. Smudin, Waterbury; Walter Nudenberg, Newtown, all of Conn.

[73] Assignee: Uniroyal Chemical Company, Inc., Middlebury, Conn.

[21] Appl. No.: 530,336

[22] Filed: Sep. 8, 1983

[51] Int. Cl.$^4$ .............................................. C07C 3/21
[52] U.S. Cl. ..................... 585/511; 526/206; 526/226
[58] Field of Search .............. 585/511, 522, 532; 526/206, 226

[56] References Cited

U.S. PATENT DOCUMENTS

| | | | |
|---|---|---|---|
| 3,413,376 | 11/1968 | Cleary et al. | 585/522 |
| 3,629,150 | 12/1971 | Addy | 585/522 |
| 4,017,553 | 4/1977 | Cesca et al. | 585/533 |
| 4,041,098 | 8/1977 | Loveless | 585/524 |
| 4,071,575 | 1/1978 | Morikawa et al. | 585/511 |
| 4,087,379 | 5/1978 | de Hault et al. | 585/533 |
| 4,469,910 | 9/1984 | Loveless | 585/511 |

*Primary Examiner*—D. E. Gantz
*Assistant Examiner*—A. Pal
*Attorney, Agent, or Firm*—John A. Shedden; William E. Dickheiser

[57] ABSTRACT

A process for oligomerizing alpha-olefins comprising contacting in a reactor zone under reaction conditions: (a) alpha-olefins having at least three carbon atoms; (b) an alkyl aluminum bromine or iodine compound having the formula $R_3Al_2X_3$ or $R_nAlX_{3-n}$, wherein n is 1 or 2; R is an hydrocarbyl group and X is a reactive halogen selected from bromine and iodine; and (c) a cocatalyst which is (i) bromine, (ii) iodine, (iii) hydrocarbyl bromide having at least one halogen group reactive with said aluminum compound or (iv) hydrocarbyl iodide having at least one halogen group reactive with said aluminum compound.

5 Claims, No Drawings

METHOD FOR THE OLIGOMERIZATION OF ALPHA-OLEFINS

This invention relates to novel catalyst systems useful for polymerizing alpha-olefins and to the process in which this catalyst system is used to obtain hydrocarbon oligomers useful as lubricants, hydraulic fluids, heat transfer fluids and the like.

It is known to prepare polymeric lubricating oils by contacting an alpha-olefin with a metal halide catalyst, such as $AlCl_3$ and limiting the extent of polymerization to between about 10 and 20 percent conversion of monomer to polymer as disclosed in U.S. Pat. No. 2,559,984. Unless such commercially unattractive low conversions are maintained, products having poor viscosity index and high pour point are obtained. The instant invention utilizes soluble catalysts and produces, in high conversion, oligomers having high viscosity index and excellent low temperature viscosity.

It is also known to obtain synthetic lubricating oils by contacting one or more alpha-olefins in the $C_6$–$C_{14}$ range at a temperature of about 0° to 50° C. with a catalyst system formed from three components: (a) alkyl aluminum sesquichloride, dialkyl aluminum monochloride or monoalkyl aluminum dichloride; (b) titanium tetrachloride; and (c) an oxygen-containing organic compound which is either an oxirane or a methyl allyl ether. Such a process is disclosed in U.S. Pat. No. 3,206,523.

U.S. Pat. No. 3,179,711 discloses a similar method wherein the third component is tetra-alkyl silicate rather than an oxygen-containing hydrocarbon compound.

The catalysts described in the above patents are characterized by their slow polymerization rate (for example, twenty hours are frequently required for high monomer conversion) and frequent necessity for using solvents.

The instant invention provides a process where the reaction rates of the catalyst are very rapid and the use of solvent is not necessary. These features lend themselves to the rapid production of oligomer in a batch or continuous process. The highly desirable continuous process is impractical when the above catalysts of the prior art are used.

The preparation of synthetic lubricating oils by polymerizing an alpha-olefin with $AlCl_3$ at 57° C. has also been revealed to produce, e.g., a polyoctene having a viscosity index of 104 and a pour point of $-20°$ F. (Industrial and Engineering Chemistry, Vol. 23, No. 6, June, 1931, pp. 604–611.)

A method for producing lubricating oils by treating a petroleum distillate containing a high percentage of unsaturated hydrocarbons in the presence of $AlCl_3$ at a temperature of between 300° and 400° F. has also been disclosed in U.S. Pat. No. 1,309,432.

According to the instant invention, aluminum alkyls may be dissolved in the alpha-olefin monomer and the solution, then fed to a reaction zone in a continuous process. The monomer to aluminum ratio can be held constant throughout the polymerization in the process according to the instant invention.

U.S. Pat. Nos. 3,637,503 and 2,525,788 describe the preparation of alpha-olefin oligomers utilizing aluminum halides activated by hydrohalide acids. These catalysts are insoluble in the monomer, and the described methods are batch polymerizations involving hydrocarbon solvents and long reaction times, none of which are limitations of the present method.

Other prior art describing variations of the above aluminum halide processes are U.S. Pat. No. 4,066,715 and German Offen. No. 2,617,403.

U.S. Pat. No. 4,041,098 describes a method for oligomerizing alpha-olefins utilizing a catalyst prepared by combining alkyl aluminum chlorides with a variety of alkyl halides in the presence of alpha-olefin. The main teaching of this patent lies in the preparation of relatively low molecular weight oligomers ($C_{20}$ to $C_{60}$) in reasonable conversion. It points out that polymerizations having a high proportion of oligomer greater than $C_{60}$ result in products which have pour points too high to be useful. The preferred polymerization temperature disclosed in the reference is 100°–140° C. The alkyl halides disclosed are chlorides, bromides or iodides wherein not more than one halogen is attached to any single carbon in the molecule. In this process, low boiling oligomers are removed by distillation and the resulting product is optionally hydrogenated to improve its oxidative stability.

It would be advantageous to oligomerize alpha-olefins at high conversion utilizing a method and catalyst wherein continuous polymerization can be performed easily, where molecular weight can be controlled by temperature and catalyst concentration and where very low halogen content oligomers can be obtained if desired. The instant invention provides polymerization methods wherein all these advantages can be attained. This combination of advantages is not taught or suggested in any of the prior art methods.

High and low viscosity alpha-olefin oligomers are known to be useful in the production of functional fluids such as lubricants. Low viscosity oligomers (e.g., having kinematic viscosity from 4 to 30 cSt at 100° C.) are frequently used as the main base stock for synthetic lubricants, frequently with the addition of a thickener which can be a high molecular weight rubbery viscosity index (V.I.) improver or a viscous oil. More viscous poly-alpha-olefins (e.g., 40–1000 cSt at 100° C.) are generally added to low viscosity natural or synthetic fluids to increase their viscosity to a given S.A.E. grade, while also frequency improving their viscosity index. The present invention teaches how catalyst changes permit production of a very wide viscosity range of products useful either as base stock or as thickeners.

According to the present invention, synthetic hydrocarbon fluids are prepared by contacting one or more alpha-olefin monomers with a soluble catalyst system prepared by reacting in the presence of monomer a trialkyl aluminum, an alkyl aluminum bromide or an alkyl aluminum iodide with bromine, iodine or an organo-bromide or organo-iodide. The three necessary ingredients may be brought together into the reactor means in any convenient manner with the restriction that monomer must be present when the aluminum compound and cocatalyst are contacted. Any operator skilled in the art can easily assess that there are several variations possible by which the ingredients may be combined. Thus, for instance, monomer, aluminum compound and cocatalyst can all be directed separately into the reaction means or one or both of the catalyst ingredients can be dissolved in all or part of the monomer prior to contacting in the reactor means. The operation of this invention requires that the overall halogen to aluminum ratio should be at least 2.5 to 1. Normally the level of aluminum compound utilized is such that the molar ratio of monomer to aluminum is from 20 to 200. The halide cocatalyst usage is regulated, as dictated by the aluminum level, to achieve an overall active halogen to aluminum ratio of at least 2.5 to 1 or higher. A convenient procedure for performing the invention is to dissolve the organo-aluminum compound in an alpha-olefin and combine it with a solution of organo halide compound also in the alpha-olefin. The combining can take place, for example, in a stirred autoclave or a pipe reactor. Reaction to form the product is very rapid and continuous polymerization can be achieved by removing reaction mixture at the same rate the feed ingredients are being introduced.

Longer residence times in the reactor may be used for producing higher viscosity oligomers which is accomplished by increasing reactor size for a given feed rate or reducing feed rate for a given reactor size, or by cooling the reaction mass.

Conversely, with a given catalyst composition, low residence times and higher temperatures can be utilized to produce low viscosity fluids.

Monomer consumption is normally greater than 95% and usually greater than 99%. The reaction may be stopped with water or a low molecular weight alcohol, followed by a catalyst removal step, such as an aqueous wash. Other methods of catalyst removal, such as filtration, absorption or centrifugation can also be utilized. The product is usually subjected to an evaporative distillation to remove unreacted monomer or low boiling oligomers (e.g., below $C_{25}$) thereby insuring low volatility in the final product. The oil is optionally hydrogenated before or after distillation by conventional methods employing a hydrogenation catalyst and hydrogen for production of fluids having improved oxidation stability. Normally, an iodine number below 5 and preferably below 2 will produce an oligomer with excellent oxidation stability as illustrated in U.S. Pat. No. 4,110,234.

The alkyl aluminum compounds operable in this invention are of the formula $R_3Al_2X_3$ or $R_nAlX_{3-n}$ where:

X is Br or I, n is 1, 2 or 3, and R is $C_1$–$C_{12}$ alkyl e.g., methyl, ethyl, propyl, i-propyl, butyl, i-butyl, hexyl, octyl, decyl or dodecyl, or phenyl, tolyl and the like.

The halogen cocatalysts operable in the invention are $Br_2$, $I_2$, organo bromides or organo iodides having one or more reactive halogen atom per molecule. Aromatic halides are not operable. The organo halides can be primary, secondary or tertiary aliphatic compounds, allylic halides or benzylic halides. Typical of such halides are t-butyl bromide; t-butyl iodide; alkyl bromide; allyl iodide; 1,2-dibromobutane; 2,3-dibromobutane; 3,4-dibromopentane; 1,4-dibromobutene-2; 1,4-diiodobutene-2; 1,2-dibromocyclohexane; methallyl bromide; methallyl iodide; benzyl bromide; benzyl iodide; 1,2,7,8-tetrabromooctane; 1-bromo-2-phenylethane; 1,2-dibromo-1-phenylethane; 1,2,5,6-tetrabromo-cyclooctane and the like. Also usable as organo halide cocatalysts are higher molecular weight saturated or unsaturated molecules which have been halogenated to contain an average of one or more bromine or iodine atom per molecule, for instance, brominated mineral oil, brominated high molecular weight poly-alpha-olefins, brominated wax or brominated rubbers or plastics providing the resultant products have solubility in alpha-olefins.

The monomers of use in this invention are those normally polymerizable by cationic (acid) catalysis. Thus, alpha-olefins of $C_3$ to $C_{14}$ carbon atoms per molecule can be used to prepare polyalpha-olefins. Alpha-olefins from $C_6$ to $C_{12}$ are preferred in homopolymers because of their ease of handling (liquid) and the excellent properties of their oligomers. Copolymers from mixtures of alpha-olefins can also be prepared, and such methodology finds benefits particulary in blends of low molecular weight and high molecular weight monomers, whose copolymers have properties superior to mixtures of their homopolymers.

Aside from straight-chain alpha-olefins, terminal olefins with branching can be polymerized using the methods of the instant invention. For instance, useful oligomers can be made from vinylidene-type monomers, such as 2-methylpropene (isobutylene), 2-ethylhexene-1, 2-butyloctene-1 and the like. Monomers having terminal double bonds and branches remote from the unsaturation may also be easily polymerized. An example of such a monomer would be 4-methylhexene-1.

As is obvious to one skilled in the art, a variety of useful functional fluids can be prepared utilizing various mixtures of the above monomers.

As with all polymerizations involving organometallic catalysts, all ingredients and equipment used should be as free from air, moisture and other potential catalyst poisons as possible. Equipment can be dried by heat and vacuum while monomers can be distilled, passed through desiccant columns or stored over desiccants. Manipulation of the ingredients before and during polymerization should stress anaerobic conditions and inert gas atmospheres where necessary.

In practice, the level of organoaluminum compound utilized should be at least 0.1% by weight of the total monomer. The halogen or organohalide useage should be such to provide an ultimate total active halogen to aluminum ratio of at least about 2.5/1. The halogen to aluminum ratio is calculated as the mole ratio of active halogen to aluminum in the total system; thus, in $R_3Al_2X_3+3RX$, $X/Al=3/1$ and in $R_3Al+4RX$, $X/Al=4/1$ where X and R are defined as above.

While there is no upper limit on the amount of either catalyst component, little is gained by utilizing greater than 5% by weight of the organometallic compounds or by operating at halogen to aluminum ratios greater than 25/1.

The temperature operative in the practice of this invention normally range from 0° C. to 200° C., although temperatures outside this range can be utilized. In non-adiabatic polymerizations, heat transfer capability may be necessary to maintain steady state conditions.

The invention is further illustrated by and will become more clear from a consideration of the following examples which should not be construed to limit the scope of the invention.

EXAMPLE I

This example illustrates the preparation of an oligomer of decene-1 utilizing a catalyst combination containing bromine as the sole halogen.

A dry, nitrogen filled, 4-necked, 500 ml round bottomed flask was fitted with:

(1) a thermometer;
(2) a 125 ml dropping funnel having a pressure equalizing side arm and a stopper;
(3) a similar dropping funnel connected to a nitrogen source and bubbler to insure a slight nitrogen pressure in the flask; and (4) an overhead mechanical stirrer.

Beneath the flask was placed a bath of cold water on a jack permitting cooling of the flask when necessary.

Into dropping funnel (2) was syringed 105 ml dried decene-1, and 4.0 ml bromine were slowly added to the decene (optionally, the bromine may be added to the decene in a separate flask and then transferred to the dropping funnel).

Into dropping funnel (3) was syringed 95 ml dry decene-1 and 16 ml of a 25% solution (0.5 molar) of ethyl aluminum sesquibromide in hexane.

Bromine to aluminum ratio: 11.25 molar.

To start the oligomerization, 5 ml from funnel (3) were added to the reaction flask followed by 5 ml from funnel (2). In a short time, reaction initiated as evidenced by a sudden exotherm and the formation of yellow color. To the now viscous oil in the flask the contents of funnels (2) and (3) were added at equal rates with vigorous stirring, such that the entire contents of the funnels were added within 90 minutes. Thus the combined feed rate was 2.22 ml per minute. During the addition period, temperature was maintained at 42° C.±2° C. by raising or lowering the water bath below the flask.

After addition of the reactants was completed, the reaction mixture was stirred for an additional 15 minutes. The catalyst was then destroyed by the addition of 5 ml of methanol. The precipitated catalyst residues thus formed are removed by filtering the reaction slurry through a bed of alumina (a solvent, such as hexane may be added prior to the filtration if the oligomer is so viscous as to require inordinately long filtration times).

The clear crude oligomer is then subjected to vacuum distillation to remove any low boiling solvents, monomer or dimer remaining. Topping of the oils is accomplished by heating the body of the oil to about 270° C. at a vacuum of about 0.1 millimeters. Usually the maximum head temperature observed is about 170° C.

The product was a viscous pale yellow oil having a kinematic viscosity of 82.86 cSt at 100° C., 939.72 cSt at 40° C., and a viscosity index of 170.

It will be shown in later examples that the viscosities attained with this bromine based soluble catalyst are higher than prior art soluble chlorine based catalysts.

EXAMPLE II

This example illustrates the effect of catalyst level in an oligomerization as in Example I, except that 4 ml of 25% ethyl aluminum sesquibromide (EASB) was added to funnel (3) and only one ml of bromine was added to funnel (2).

The product oligomer (produced in 95% yield) had a kinematic viscosity at 100° C. ($KV_{100}$) of 43.41 cSt, a $KV_{40}$ of 323.72 cSt, and a V.I. of 150.

Thus, examples I and II show the profound change in viscosity obtained when catalyst level is reduced from 2% by weight on monomer of EASB in Example I to 0.5% in Example II. No other process changes were required.

EXAMPLE III

This example illustrates the effect of temperature on the viscosity of the oligomeric products. In this polymerization, 16 ml of 25% EASB and 3 ml of $Br_2$ were utilized (Br/Al=8.8) and, in order to attain a higher reaction temperature, the ingredients were combined over a 30 minute period (6.66 ml per minute). The temperature was maintained at 72°±2° C. for the duration of the addition. The product work-up was as in Example I. The oligomer had $KV_{100}$ of 35.05 cSt, $KV_{40}$ of 344.74 cSt, and a V.I. of 146.

This illustrates that rapid addition and higher temperature utilizing 2% EASB produces a product similar to that made in Example II where less catalyst and slower feed rates were employed.

EXAMPLE IV

This example illustrates the effect of addition rate on the viscosity of oligomers produced by the catalyst of this invention.

Example III was repeated, except that the cooling bath was utilized to maintain reaction temperature at 42°±2° C. The final product had a $KV_{100}$ of 60.87 cSt. The increased rate of addition lowered viscosity as compared with Example I, while the lower temperature of polymerization increased the viscosity as compared with Example III.

Table I below is a summary of the first four examples and illustrates how the viscosity of oligomers can be varied by changes in addition rate, temperature and catalyst concentration while maintaining exactly the same process and catalyst combination.

TABLE I

| EXAMPLE | % EASB | Reaction Temperature, °C. | Addition Rate, ml/min. | $KV_{100}$, cSt |
|---|---|---|---|---|
| I | 2 | 42 ± 2 | 2.22 | 82.86 |
| II | 0.5 | 42 ± 2 | 2.22 | 34.41 |
| III | 2 | 72 ± 2 | 6.66 | 35.05 |
| IV | 2 | 42 ± 2 | 6.66 | 60.87 |

EXAMPLE V

This example illustrates the use of trialkyl aluminum compounds as substitutes for the EASB of Example I. Trialkyl aluminum compounds are readily soluble in hydrocarbon and are of lower acidity than alkyl aluminum halides, such as EASB. Under certain conditions, monomers such as decene containing dissolved alkyl aluminum halides can undergo spontaneous polymerization in the presence of adventitious water. This unwanted and even dangerous reaction can be completely avoided by the use of trialkyl aluminums. Thus, following the procedure of Example 1, 16 ml of a 1.6 molar solution of triethyl aluminum (TEA, 0.0256 mol) was dissolved in decene in funnel (3) and 4.19 ml bromine was added to decene in funnel (2) to give an overall Br/Al ratio of 6.36. Oligomerization was initiated by adding 0.5 ml of 25% EASB and 5 ml from funnel (2) to the reaction flask. This was necessary because of the reluctance of pure trialkyl aluminum to react with certain alkyl bromides at ordinary temperatures. Reaction was nearly instantaneous, and thereafter funnels (2) and (3) were added as in Example I. The product oligomer had $KV_{100}$ of 107.07 cSt and a V.I. of 178.

EXAMPLE VI

Example V was repeated, except that 0.0256 moles of triisobutyl aluminum was used in place of the triethyl aluminum. Surprisingly, the product has a $KV_{100}$ of only 43.83 cSt. This indicates that viscosity control of oligomers is possible with trialkyl aluminum based catalysts.

EXAMPLE VII

In this example, a solution of allyl bromide in decene, instead of the bromine of Example I, is reacted in the reaction flask with a solution of EASB in decene.

Thus 16 ml of 25% EASB (0.5 molar) in hexane was dissolved in 93 ml decene-1 in funnel (3), and 2.9 g allyl bromide (0.024 moles) was dissolved in 107 ml decene-1 in funnel (2) to give a Br/Al ratio of 3/1. The ingredients in funnels (2) and (3) were combined as in Example I over a period of 90 minutes while maintaining 30±2° C. After work-up and distillation as in Example I, the product oligomer had a $KV_{100}$ of 57.9 cSt and a V.I. of 158.

EXAMPLE VIII

In this example, 1,2-11,12-tetrabromodecane is used as a cocatalyst with EASB to prepare an oligomer of decene.

Accordingly, 4 ml (78 mmol) $Br_2$ were reacted in a 100 ml Erlenmeyer flask with 5.38 g (39 mmol) 1,9-decadiene to produce 17.86 g of 1,2,11,12-tetrabromodecane. This was dissolved in 100 ml decene-1 in funnel (2). Thereafter, the polymerization reaction was performed as in to Example I. The resultant oligomer was nearly identical to that produced in Example I, having a $KV_{100}$ of 79.36 cSt, a $KV_{40}$ of 913.93 cSt and a V.I. of 167.

Thus, organic halides having a multiplicity of halogen atoms per molecule are operative in this invention.

EXAMPLE IX

This example illustrates the use of tertiary butyl bromide as a cocatalyst with triethyl aluminum to prepare an oligomer of decene.

The polymerization was run as in Example I, except that funnel (2) contained 12.3 ml (14.6 g) t-butyl bromide dissolved in 109.2 ml decene-1 and funnel (3) contained 20.8 ml of a 1.25 normal triethyl aluminum (TEA) in hexane solution dissolved in 95.8 ml decene-1. The product oligomer had a $KV_{100°\ C.}$ of 126 cSt, a $KV_{40°\ C.}$ of 1539 cSt and a V.I. of 182.

Thus tertiary aliphatic bromides are operative in this invention and produce oligomers of high viscosity.

EXAMPLE X

This example illustrates the use of 2,3-dibromobutane, readily prepared by the addition of bromine to butene-2.

Thus, in a polymerization run as in Example I, 3.3 ml (5.94 g) of 2,3-dibromobutane were added to 108.5 ml decene in funnel (2) and 10.4 ml of 1.25N TEA were added to 96.5 ml decene-1 in funnel (3). Reaction was initiated with EASB as in Example V, and the polymerization continued by adding the ingredients in funnels in (2) and (3) as in Example I. The resultant product had a $KV_{100}$ of 82.5 cSt and a V.I. of 165.

EXAMPLE XI

The use of aluminum alkyl iodides with organo iodides as catalysts for the oligomerization of alpha-olefins is illustrated in this example.

In a polymerization performed basically as in Example I, 14.8 ml of a 25 wt. % hexane solution of ethyl aluminum sesquiiodide ($Et_3Al_2I_3$) was added to 95 ml decene-1 in funnel (3), and 5.86 g allyl iodide was added to 105 ml decene-1 in funnel (2). The I/Al ratio was 4. The ingredients in funnels (1) and (2) were added over a period of 90 minutes, while maintaining the temperature at 50°±2° C. Product viscosity: $KV_{100}$=9.3 cSt, V.I.=145.

Thus, it is demonstrated that catalyst combinations of aluminum alkyls and organic iodides containing no other halogen atoms produce very low viscosity fluids not attainable with all bromine or all chlorine systems.

EXAMPLE XII

This example demonstrates the use of molecular iodine as a cocatalyst. It also illustrates the use of a catalyst combination containing both bromine and iodine.

The apparatus used in this example was identical to that in Example I. In this example, 6.1 g of iodine was added directly to the reaction flask. Funnel (2) contained 100 ml of decene-1 and funnel (3) contained 16 ml of a 25% hexane solution of EASB in 100 ml decene-1. Five ml from funnel (3) were added, and reaction was immediate. Thereafter, the contents of funnels (2) and (3) were added over a 90 minute period while maintaining a temperature of 42°±2° C. The product (worked up as in Example I) had a $K.V._{100}$ of 18.86 cSt and a V.I. of 136.

The viscosity attained is intermediate to that of the all bromine catalyst of Example I (82.86 cSt) and the all iodine catalyst of Example XI (9.3 cSt).

EXAMPLE XIII

This example compares the bromine based and iodine based catalysts of this invention with similar chlorine based catalysts as described in U.S. Pat. No. 4,041,098. All polymerizations were performed as described in Example I (Run C is outside this invention):

| Run | Aluminum Alkyl | Alkyl Halide | Halogen/Al Ratio | $K.V._{100}$ cSt | V.I |
|---|---|---|---|---|---|
| A. | $Et_3Al_2Br_3$ | $CH_2=CHCH_2Br$ | 3/1 | 65.8 | 156 |
| B. | $Et_3Al_2I_3$ | $CH_2=CHCH_2I$ | 3/1 | 9.3 | 145 |
| C. | $Et_3Al_2Cl_3$ | $CH_2=CHCH_2Cl$ | 4/1 | 42.58 | 146 |

The surprising difference among these three catalyst systems was not recognized in U.S. Pat. No. 4,041,098, which dealt only with alkyl aluminum chlorides. Unexpectedly, the ordering of viscosities of the oils produced by these catalysts does not follow the logical sequence expected from the relationship of chlorine, bromine and iodine in the Periodic Table. That is, while it is surprising that catalysts based on only one halogen produce different viscosities, it is even more surprising that the viscosities produced are not ordered in a Cl, Br, I or an I, Br, Cl sequence.

Furthermore, the instant invention exemplifies the use of trialkylaluminum compounds with which much higher viscosities can be made, as shown in Example V. The use of trialkyl aluminum compounds is not taught in U.S. Pat. No. 4,041,098. It has been shown, in Examples V and IX, for instance, that the use of triethyl aluminum with alkyl bromides produces oligomers of higher viscosity than are attainable with alkyl aluminum chlorides or trialkyl aluminum compounds with alkyl chloride cocatalysts under comparable conditions. Oligomerization of decene with triethyl aluminum and tertiary butyl chloride produces a fluid having $KV_{100}$ of 20.38 cSt, far less than the $KV_{100}$ of 126 cSt as described in Example IX.

EXAMPLE XIV

This example illustrates the use of ethyl aluminum sesquibromide in combination with 2,3-dibromobutane as a catalyst for the oligomerization of decene-1.

In a polymerization conducted as in Example I, funnel (3) was loaded with 97.8 ml decene-1 and 8 ml of 25% EASB hexane solution, while funnel (2) was loaded with 102.2 ml decene-1 and 3.6 ml 2,3-dibromobutane.

After reaction and work-up, the product had a K.V.$_{100}$ of 51.8 cSt and a V.I. of 154.

EXAMPLE XV

This example illustrates the use of EASB in combination with tertiary butyl bromide as a catalyst for the oligomerization of decene-1.

In a polymerization conducted as in Example I, 15.3 ml of a 25% hexane solution of EASB were dissolved in 93.8 ml decene-1 in funnel (3), and funnel (2) was loaded with 2.8 ml tertiary butyl bromide in 106.2 ml decene-1.

After reaction and work-up, the product had a K.V.$_{100}$ of 26.8 cSt and a V.I. of 150. This example, when compared with Example 9, illustrates the profound influence of the type of aluminum alkyl employed in the catalyst.

EXAMPLE XVI

This example illustrates the use of 1,4-dibromobutene-2 with triethyl aluminum as a catalyst for decene-1 oligomerization.

In a polymerization conducted as in Example-1, solutions of 20.8 ml of 1.25N triethyl aluminum in 92.8 ml decene-1 and 6.3 ml 1,4-dibromobutene-2 in 112.2 ml decene-1 were combined over a 90 minute interval at a temperature of 42°±2° C. After work-up as in Example I, the product had a K.V.$_{100}$ of 38 cSt and a V.I. of 146.

EXAMPLE XVI

This example illustrates the polymerization of decene-1 by direct interaction with EASB and elemental bromine.

To the apparatus as described in Example I was added a "Y" tube, which permits the use of a third dropping funnel. Into funnel (2) was placed 95 ml dry decene-1 and 16 ml of 1 25% solution of EASB in hexane. Into funnel 3 was placed 105 ml decene. In the third funnel (placed so it feeds directly into the reaction mixture), was put 4.0 ml bromine. The contents of all three funnels were combined at such rates that the overall addition required 90 minutes. That is, while the ingredients from funnel (2) and (3) were added at about 1.2 ml per minute each, the bromine was added at the rate of about 0.44 ml every ten minutes for 90 minutes. Polymerization proceeded, and the product had a K.V.$_{100}$ of 79.8 cSt. This example illustrates that bromine need not be pre-reacted with olefins. This procedure also permits greater versatility in that Br/Al ratios can be changed upward or downward (during a monitored polymerization) to promote in process viscosity adjustments.

EXAMPLE XVII

This example illustrates the use of still further alkyl halides operable in the invention. Thus, in a polymerization run exactly as in Example I, the following alkyl bromides were found to be active cocatalysts with EASB. The amount of alkyl bromide introduced into funnel (2) was adjusted so that the overall Br/Al ratio in the system was 4 and the level of EASB employed was as in Example I.

The following alkyl bromides were found to react readily with EASB in the presence of decene to produce oligomers essentially of the same viscosity and V.I.'s as described in the previous examples: 3-bromobutene-1; 2,3-dibromo-2,5-dimethylhexene-3; 2,5-dibromo-2,5-dimethylhexene-3; benzyl bromide; alpha-bromoethylbenzene; and alpha, alpha'-dibromo-p-xylene.

What is claimed is:

1. A process for oligomerizing alpha-olefins comprising contacting in a reaction zone under reaction conditions:
   (1) Alpha olefins having at least three carbon atoms; and
   (2) A catalyst composition consisting essentially of (a) an alkyl aluminum bromide or iodide compound having the formula $R_3Al_2X_3$ or $R_nAlX_{3-n}$, wherein n is 1; R is an hydrocarbyl group and X is a reactive halogen selected from bromine and iodine; and (b) a cocatalyst which is selected from the group consisting of alkyl iodide and alkyl bromide.

2. The process of claim 1 wherein the overall molar ratio of reactive halogen to aluminum is at least 2.5.

3. The process of claim 2 wherein the overall molar ratio of monomer to aluminum is at least 3.8.

4. The process of claim 3 wherein the overall molar ratio of monomer to aluminum is at least 10.

5. The process of claim 4 wherein the overall molar ratio of monomer to aluminum is from 20 to 200.

* * * * *